United States Patent
Van Eeuwijk et al.

[11] Patent Number: 5,960,102
[45] Date of Patent: Sep. 28, 1999

[54] X-RAY IMAGE PROCESSING METHOD AND DEVICE FOR PERFORMING THAT METHOD IN WHICH A PORTION CORRESPONDING TO AN X-RAY ABSORPTION FILTER IS SELECTIVELY PROCESSED

[75] Inventors: Alexander H.W. Van Eeuwijk; Steven Lobregt, both of Eindhoven, Netherlands; Raoul Florent, Valenton; Jacques Breitenstein, Saint-Maur-des-Fosses, both of France

[73] Assignee: U.S. Philips Corporation, New York, N.Y.

[21] Appl. No.: 08/715,255

[22] Filed: Sep. 16, 1996

Related U.S. Application Data

[63] Continuation of application No. 08/279,761, Jul. 22, 1994, abandoned.

[30] Foreign Application Priority Data

Jul. 22, 1993 [EP] European Pat. Off. ............ 93401908
Jul. 22, 1993 [FR] France ............................. 93 09052

[51] Int. Cl.$^6$ .................................................. G06K 9/00
[52] U.S. Cl. .................... 382/128; 382/199; 382/260; 378/160; 378/901
[58] Field of Search .................................... 382/132, 128, 382/130, 199, 260, 266; 378/160, 901

[56] References Cited

U.S. PATENT DOCUMENTS

| 4,670,896 | 6/1987 | Klausz | 378/156 |
| 4,851,984 | 7/1989 | Doi et al. | 382/132 |
| 4,935,946 | 6/1990 | Hefter et al. | 378/99 |
| 5,282,254 | 1/1994 | Chiu et al. | 382/199 |

FOREIGN PATENT DOCUMENTS

| 0309813 | 4/1989 | European Pat. Off. | H05G 1/60 |
| 0523771 | 1/1993 | European Pat. Off. | G06F 15/62 |

*Primary Examiner*—Leo H. Boudreau
*Assistant Examiner*—Matthew L. Bella
*Attorney, Agent, or Firm*—Dwight H. Renfrew, Jr.

[57] ABSTRACT

An image processing method is provided to remove areas from an image made by x-irradiation, said areas corresponding to absorption filters in the x-ray beam. Because such filters, also known as x-ray shutters, are inserted into the x-ray beam from the outside of the x-ray beam, x-ray shutter-areas extend from the periphery of the image. Therefore, once the edge of an x-ray shutter-areas has been determined, the part of the image located between the periphery and the x-ray shutter-edge is removed. X-ray shutter-edges are determined by locating transition-points in the image having brightness-transitions having maxima of both the first and second spatial derivatives of the brightness-value. An x-ray shutter-edge is then determined by fitting a curve through the transition-points. The curve fitting is performed with the use of weight-factors that are representative of the likelihood that a transition-point is on an actual x-ray shutter-edge. This likelihood is larger for transition-points which are closer to the periphery of the image, for transition-points having low image roughness towards the periphery of the image. Furthermore, a transition-point having a large height of its brightness-transition is more likely to be on an actual x-ray shutter-edge.

21 Claims, 5 Drawing Sheets

X-RAY IMAGE PROCESSING METHOD AND DEVICE FOR PERFORMING THAT METHOD IN WHICH A PORTION CORRESPONDING TO AN X-RAY ABSORPTION FILTER IS SELECTIVELY PROCESSED

This is a continuation of application Ser. No. 08/279,761 filed Jul. 22, 1994, now abandoned.

BACKGROUND OF THE INVENTION

1. Field of the Invention

The invention relates to an image processing method formed by x-ray imaging, and containing a portion corresponding to an x-ray absorption filter. The invention also relates to an image processor to process an image formed by x-ray imaging, which contains a portion corresponding to an x-ray absorption filter. The invention further relates to an x-ray examination apparatus comprising an x-ray absorption filter between an x-ray detector and an x-ray source for irradiating an object to form an x-ray image on the x-ray detector.

2. Description of the Related Art

An image processing method of said kind is known from the U.S. Pat. No. 4,670,896; therein are disclosed an x-ray examination apparatus and the use thereof to form on the x-ray detector the x-ray image containing a portion corresponding to the x-ray absorption filter.

The cited reference teaches that a substantial difference in image-contrast can occur between parts of an x-ray image formed due to irradiation of the object by x-rays. Brightness differences forming image contrast arise e.g. in peripheral angiography because part of the x-ray beam does not penetrate the object, notably a patient to be examined, and is incident directly on the x-ray detector, or for example in cardio-examination because the object exhibits substantial differences in x-ray absorption, viz. a patient's heart having comparatively high x-ray absorption is surrounded by lung-tissue which is relatively transparent for x-rays. In order to make the dynamic range of the x-ray image coincide as well as possible with the contrast in the region of interest, x-ray absorption filters e.g. having the form of x-ray shutters, are arranged between the x-ray source and the object. The x-ray shutters are positioned to intercept a part of the x-ray beam so as to shield relatively transparent parts of the patient's anatomy from the x-rays. The use of such x-ray shutters leads to diminishing the x-ray dose to which a patient is exposed to produce an x-ray image. Moreover, an x-ray dose whereto a person who operates the x-ray examination apparatus is unintentionally exposed is diminished by the use of x-ray image x-ray shutters appear as regions having extremely high absorption. Consequently, in inverted images, as are often used by radiologists for examination, x-ray shutters appear as bright areas which distract attention from medical information. Furthermore, when a plurality of images made by x-ray irradiation is brought together onto a hard copy, such as an x-ray film, a substantial portion of the area of the x-ray film is wasted when said images contain areas corresponding to x-ray shutters. Thus, making images, in accordance with the cited reference, by irradiating an object by an x-ray beam and employing the x-ray absorption filter arranged between the x-ray source and the x-ray detector has several shortcomings and disadvantages.

SUMMARY OF THE INVENTION

Therefore, it is an object of the invention to provide an image processing method for reducing harmful effects of areas in the image corresponding to the x-ray absorption filter on the quality of the image made by x-irradiation.

This object is achieved by the image processing method according to the invention to process an image formed by x-ray imaging, the image containing a portion corresponding to an x-ray absorption filter, characterized in that the image processing method comprises modifying the image by selectively processing said portion.

A processed image that does not show harmful effects such as distracting features in the portion corresponding to the x-ray absorption filter appearing in the image as x-ray shutter-areas is obtained in accordance with the image processing method of the invention since portions of the x-ray image corresponding to an x-ray absorption filter i.e. for instance x-ray shutter-areas are modified for example in that these are removed from the image. Then in the processed image the portion corresponding to an x-ray shutter area is absent. Pixel-values in the x-ray shutter-area may also be set to a predetermined grey-level or are given a non-distracting uniform color-value. Therefore, in the processed image the portion that corresponds to x-ray shutter-areas is presented as an area having a non-distracting grey-tone or inconspicuous color and consequently the processed image only contains image information that is relevant.

It is a further object of the invention to provide an image processing method for identifying the portion corresponding to an x-ray absorption filter before selectively processing the image portion which corresponds to the x-ray absorption filter.

A preferred implementation of an image processing method in accordance with the invention is characterized in that the processing comprises determining an edge of the portion for selecting said portion as a part of the image between the edge and a periphery of the image.

Sections of the x-ray beam that are absorbed by the x-ray absorption filter may have a complicated shape corresponding to complicated anatomical structures of a patient to be examined. Therefore it is difficult and often quite impossible to know beforehand or predict the location of an area which forms the portion of the image corresponding to said filter, i.e. an area of the image in which x-rays were absorbed due to the x-ray shutters. In accordance with the invention an image processing method is provided that can be performed independently of the x-ray examination apparatus and/or adjustments thereof that is employed to irradiate the object. Furthermore, it is often desired to process the image separately from the x-ray examination. Any information regarding x-ray shutter-positions and/or adjustment will then be lost.

In images made by x-irradiation of an object one or several x-ray shutters are employed for avoiding overexposure in parts having low absorption and being irrelevant from a medical point of view. Such x-ray shutters are without exception inserted into the x-ray beam from the edge of the x-ray beam towards the center thereof. Consequently, when the location of the edge of an x-ray shutter is determined it is certain that the entire region of the image from said edge towards the periphery of the image is an x-ray shutter-area, i.e. an area in the image where x-radiation has been absorbed by the absorption filters.

When locations of edges of x-ray shutter-areas have been determined, a processed image wherein x-ray shutter-areas are reduced in that said x-ray shutter-areas are converted into a simpler form by deleting image information of x-ray shutter-areas or by setting pixel-values in areas peripheral to the x-ray shutter-edges to a predetermined grey-level or a non-distracting color-value. A processed image that does not have distracting features in x-ray shutter-areas is obtained in accordance with the image processing method of the invention by removing substantially all information content in the x-ray shutter areas since x-ray shutter-areas are removed from the image and/or pixel-values in the shutter-area are set to a predetermined grey-level or color-value. Therefore, in the processed image regions that correspond to x-ray shutter-areas are presented as parts having a non-distracting grey-tone or inconspicuous color and consequently the processed image only contains image information that is relevant.

A preferred implementation of an image processing method in accordance with the invention is characterized in that the processing comprises removing at least a part of said shutter-areas from the image.

A particular advantage of removing portions of the x-ray shutter-areas is achieved when a collection of processed images are brought together on a hard-copy, e.g. an x-ray film. As irrelevant x-ray shutter-areas are discarded, less space on the x-ray film is required, so that on the same area of the x-ray film more images can be collected.

A further preferred implementation of an image processing method according to the invention is characterized in that the processing comprises assigning substantially uniform values to pixels in the portion in the image.

Distracting portions in the image are avoided in that x-ray shutter-areas which do not contain relevant medical information are converted into portions having a uniform grey-tone or an inconspicuous color. Then the processed image is suitable to be considered by a physician who may comfortably focus his/her attention to the medical information contained in the image without being distracted by the x-ray shutter-areas.

A further preferred implementation of an image processing method in accordance with the invention is characterized in that the detection of said edge comprises a grouping step to select a group of transition-points in the image having a higher brightness towards the center of the image and a lower brightness towards the periphery of the image, and a curve-fitting step to fit a curve through said group of transition-points, said curve forming a representation of said edge.

Transition-points in the image that lie on an edge of an x-ray shutter-area have high brightness towards the center of the image and low brightness towards the periphery of the image. For each edge in the image a number of transition-points are determined and grouped into groups of transition-points for respective x-ray shutter-edges. Representations of respective x-ray shutter-edges are obtained by performing a curve-fitting method for each of the groups. The result is one or a number of curves being representative for x-ray shutter-edges in the image.

A further preferred implementation of an image processing method in accordance with the invention is characterized in that the grouping step comprises a region-selection step to select a region of interest extending from a periphery of the image and a division-step to divide said region of interest into sections and a weight-assignment step to assign weights to said transition-points, a weight for a transition-point depending on image features around said transition-point and a weight for a transition-point depending decreasingly on a distance between said transition-point and said periphery.

In an image made by x-irradiation it is known beforehand that x-ray shutter-areas extend from the periphery of the image because the x-ray shutters are inserted in the x-ray beam during x-ray exposure from the outside of the x-ray beam. Consequently, it is effective to carry-out grouping of transition-points in accordance with known topology of the image. A group of transition-points being representative of an x-ray shutter-edge has transition-points located in a region of interest that extends from the periphery of the image. A brightness-transition is a necessary but not a sufficient feature of a point in the image for being on an x-ray shutter-edge. Detection of transition-points is carried-out by dividing a region-of-interest into sections, notably elongated strips. Subsequently, brightness-values are averaged in a direction perpendicular to the longitudinal axis of elongated strips. Then, one or several points having a brightness transition are determined in each of the sections. In each of the sections, the brightness-transition being closest to the periphery of the image is the most likely candidate for being on an x-ray shutter-edge. This is implemented by assigning weight-factors to brightness-transitions found in each of the sections, each weight-factors depending decreasingly on the distance between a brightness-transitions at issue and said periphery of the image.

A further preferred implementation of an image processing method in accordance with the invention is characterized in that the grouping step comprises a first-estimate step to determine a first-estimate for a position of a transition-point in a section and an accurating step to determine a transition-point from said first-estimate.

Processing speed is increased by performing a first estimate for a transition-point on the basis of a component of the image having only low spatial frequency variations of brightness-values. Such a component is obtained by performing a local spatial averaging of brightness-values in the image. After a first estimate for a transition-point has been obtained, the position of said transition-point can be determined more accurately by considering brightness-values of the image in a neighborhood of the first estimate. Thus, it is avoided to a large extent to search in vain for transition-points in regions of the image where there are no substantial brightness variations.

A further preferred implementation of an image processing method in accordance with the invention is characterized in that the weight-assignment step comprises computation of image roughness, and computation of transition-height, and computation of said weights depending on image roughness and transition height for respective transition-points.

Brightness-transitions that relate to x-ray shutter-edges are distinguished from brightness-transitions that for example relate to anatomical structures by taking image features around these transitions into account. Image roughness is defined as e.g. the statistical variance of brightness-values or e.g. the maximum of the differences of pixel-values of pixels having a predetermined distance in the image between them. It is found empirically that image-roughness is considerably lower in the low-brightness region in an image caused by an x-ray shutter. Also the height of a transition due to an x-ray shutter-edge is higher than a brightness-transition due to anatomical structures. Therefore, selection of brightness-transitions relating to x-ray shutter-edges is made more effective if the weight-factors of the brightness-transitions are made dependent on the above image features. This dependence is such that a brightness-transition having image features indicating an x-ray shutter-edge are given higher values for its associated weight-factor. There can be several transition-points in a section, then transition-points located nearer to the periphery of the image add to image-roughness for transition-points located nearer to the centre of the image. Consequently, a dependence which is decreasing with the distance between the transition-points and the periphery of the image for weight-factors for transition-points within a section is obtained.

A further preferred implementation of an image processing method in accordance with the invention is characterized in that the weight-assignment step comprises computation of first and second spatial derivatives of brightness-values near respective transition-points and employing substantial concurrence of a maximum of said first derivative with a brightness-variation and with a maximum of said second derivative at the peripheral side of said brightness-variation for selecting the position of said brightness-variation as a transition-point and assigning said weight on the basis of said concurrence.

Brightness-transitions due to x-ray shutter edges have a particular image feature that distinguishes x-ray shutter-edges from brightness transitions for example due to anatomical structures or vignetting. It is found that a brightness-transition of an x-ray shutter-edges has a maximum first spatial derivative of the brightness values near the brightness-transition in the image and has also a maximum of the second spatial derivative of the brightness values slightly peripheral to the brightness-transition in the image. This feature is employed in selection of transition-points by assigning a low weight to transition-points not having a substantial value for their maxima of first derivatives and not having a maximum second spatial derivative slightly peripheral to the transition-point.

A further preferred implementation of an image processing method in accordance with the invention is characterized in that the weight-assignment step comprises computation of first spatial derivatives of brightness-values peripheral to respective transition-points, computation of respective average brightness-value of pixels towards the center to said transition-points, computation of respective ratios of said respective first spatial derivatives and said respective average brightness-values and assigning said weights on the basis of said ratios.

An x-ray shutter-edge gives rise to a brightness-transition in the image stronger than contrast due to an anatomical structure. Another way of distinguishing an x-ray shutter-edge from anatomical structures in the image consists of considering at a transition-point a gradient of brightness-values in a direction towards the center of the image. A value of such a gradient is subsequently connected to the average brightness-values between said transition-point and a periphery of the image. If said gradient is comparatively strong and said average corresponds to high brightness then said transition-point is comparatively more likely to be on an x-ray shutter-edge. A weight for a transition-point is made dependent on the ratio of said gradient and said average, so that a transition-point is assigned a higher weight when it is likely to be on an x-ray shutter edge.

A further preferred implementation of an image processing method in accordance with the invention is characterized in that the weight assignment step is followed by a point-selection step for selecting a transition-point having the highest weight in a section and retaining only said selected transition-points in said selected group.

Processing speed of the image processing method is increased by retaining as few transition-points as possible. The transition-points that are retained should preferably be as likely as possible to be on an x-ray shutter-edge instead of being representative for anatomical structure. Such transition-points are selected by sorting transition-points of a section on the basis of their respective weights and retaining in each section only the transition-point having the highest weight in its section.

A further preferred implementation of an image processing method in accordance with the invention is characterized in that said curve-fitting step is followed by a reassigning step for reassigning a value to a weight of a transition-point in dependence on a distance between said transition-point and a curve fitted through the group whereto said transition-point belongs, and in that the curve-fitting step is reiterated employing said reassigned weight.

When anatomical structures are visible due to scatter radiation in an x-ray shutter-area, transition-points within the x-ray shutter-area may be selected in the point-selection step. The ensuing curve fitting step will then produce a curve to which selected points may have a comparatively large distance. This occurs because anatomical structures have a more complicated structure than approximately straight x-ray shutter-edges. To prevent image structures that are e.g. due to scatter radiation being mistaken for x-ray shutter-edges, weight-factors of the transition-points are decreased on the basis of said distance. Transition-points which are close to the fitted curve have a higher likelihood to be actually on the edge of an x-ray shutter-area; therefore, weight-factors of transition-points are adapted before performing a next iteration-step in correspondence with said likelihoods. The iteration is performed particularly effectively because an adequate data-set for starting the iteration is chosen as follows. For each section a peak-point is selected among the transition-points in said section. A peak-point is a transition-point that has the smallest average distance between said peak-point and a predetermined number of neighboring transition-points; empirically it has appeared that the choice of five neighboring transition-points is very adequate to determine a peak-point. The first estimate for a curve representing an x-ray shutter edge is then taken to be a curve that connects peak-points of respective sections.

A further preferred implementation of an image processing method in accordance with the invention is characterized in that the edge-determination step is followed by an edge-verification step comprising computation of a reliability-parameter for an edge being determined and comparison of said reliability-parameter with a predetermined threshold level.

Even in the cases where no x-ray shutter was employed during irradiation the image processing method in accordance with the invention may produce a curve allegedly identifying an x-ray shutter-edge. In such instances an anatomical structure would mistakenly be regarded as an x-ray shutter. To avoid such errors, an edge-verification step is performed. Anatomic structures differ from x-ray shutter-edges in that the latter give rise to comparatively straight curves. A plurality of said straight curves constitutes a, possibly complex, circumference of a section of the x-ray beam that is passed through the x-ray absorption filter. Moreover, if a curve detected in a region of interest extending from one periphery of the image indeed represents an x-ray shutter edge, then most often another x-ray shutter-edge is present in a region of interest extending from an opposite periphery of the image. An average distance of a predetermined number of transition-points generates a quantitative measure of straightness of a curve. A reciprocal of said average distance is employed as a reliability parameter. If said reliability parameter has a value below a predetermined threshold-value then it is decided that the detected curve does not for certain relate to an x-ray shutter-edge and the step of reducing the area peripheral to said curve consists of leaving the pixel-values in said area unaltered. If the reliability exceeds said threshold-value then a presence of an x-ray shutter-edge in an opposite region-of-interest is verified. If no such opposite x-ray shutter is found then the fitted curve is discarded and again the step of reducing the area peripheral to said curve consists of leaving the pixel-values in said area unaltered.

A further preferred implementation of an image processing method according to the invention is characterized in that for a plurality of transition-points said reliability parameter is computed and in a situation where comparison of said reliability parameter to said predetermined reference level indicates the presence of said portion corresponding to an x-ray absorption filter for fewer transition-points than a predetermined reference number the edge-verification step is supplemented by comparison of pixel-values of collections of pixels on different sides of the curve.

When the number of transitions point retained for fitting the curve is less than a predetermined reference number then an ambiguous situation with regard to deciding on the presence of an x-ray shutter arises. Then according to the invention the average intensities of collections of pixels on either side of the curve are compared. Should these average intensities differ more than a predetermined reference level then it is decided that an x-ray shutter is present because a high mean intensity on the side of the curve towards the center of the image and a low mean intensity on the side of the curve toward the periphery of the image is compatible with the presence of an x-ray shutter. The predetermined reference number may be set to a very high value, for instance equal to the total number of pixels of the image, in order to achieve that supplementing the edge-verification step is performed in almost any situation.

To reduce the computational burden said average intensities may be calculated for comparatively small regions in the image, for example two vertical line segments an inner one with respect to the calculated curve lying towards the center of the image and the other, outer one, lying towards the periphery of the image.

To improve the reliability of the edge verification the maximum value $L_{max}$ of the second spatial derivative (Laplacian) of the pixel-values on the outer segment is determined. If this maximum value is found to be large, it indicates the presence of a anatomical structure towards the periphery of the accurate transition-point at issue and hence the likelihood of the actual presence of an x-ray shutter is reduced.

A further preferred implementation of an image processing method according to the invention is characterized in that for a plurality of transition-points said reliability parameter is computed and in a situation where comparison of said reliability parameter to said predetermined reference level indicates the presence of said portion corresponding to an x-ray absorption filter for fewer transition-points than a predetermined reference number the edge-verification step is supplemented by determining a magnitude of a first spatial derivatives of brightness-values of pixels in the image between the curve and the periphery of the image, said derivative being negative in the direction from the curve to the periphery of the image and comparing said magnitude to a predetermined reference value.

When the number of transition points retained for fitting the curve is less than a predetermined reference number then an ambiguous situation with regard to deciding on the presence of an x-ray shutter arises. Then according to the invention the gradients of the intensities for collections of pixels on either side of the curve are compared to each other. As intensities, and thus pixel values, hardly ever decrease strongly within an x-ray shutter-area in a direction towards a periphery of the image, considering the most negative slope constitutes a reliable test for the presence of an x-ray shutter in an ambiguous situation. Strongly decreasing pixel-values peripheral from the computed curve therefore indicate that the computed curve does not represent an x-ray shutter-edge.

It is also an object of the invention to provide an image processor to process an image formed by x-ray imaging, which contains a portion corresponding to an x-ray absorption filter device and which is arranged to carry out the image processing method of the invention. This is achieved by an image processor according to the invention which is characterized in that the processor comprises a device for determining an edge of the portion and a device for modifying the image by selectively processing the portion.

Moreover, it is an object of the invention to provide an x-ray examination apparatus comprising an x-ray absorption filter between an x-ray detector and an x-ray source for irradiating an object to form an x-ray image on the x-ray detector and which is arranged to carry out the image processing method of the invention. This is achieved by an x-ray examination apparatus according to the invention, characterized in that the apparatus comprises an image processor configured for carrying out the aforementioned method and having an input port coupled to the x-ray detector.

BRIEF DESCRIPTION OF THE DRAWING

These and other aspects of the invention will become apparent from and will be elucidated with reference to the implementations and the embodiments described hereinafter and with respect to the accompanying drawings wherein.

DETAILED DESCRIPTION OF THE PREFERRED EMBODIMENTS

Figure 1:
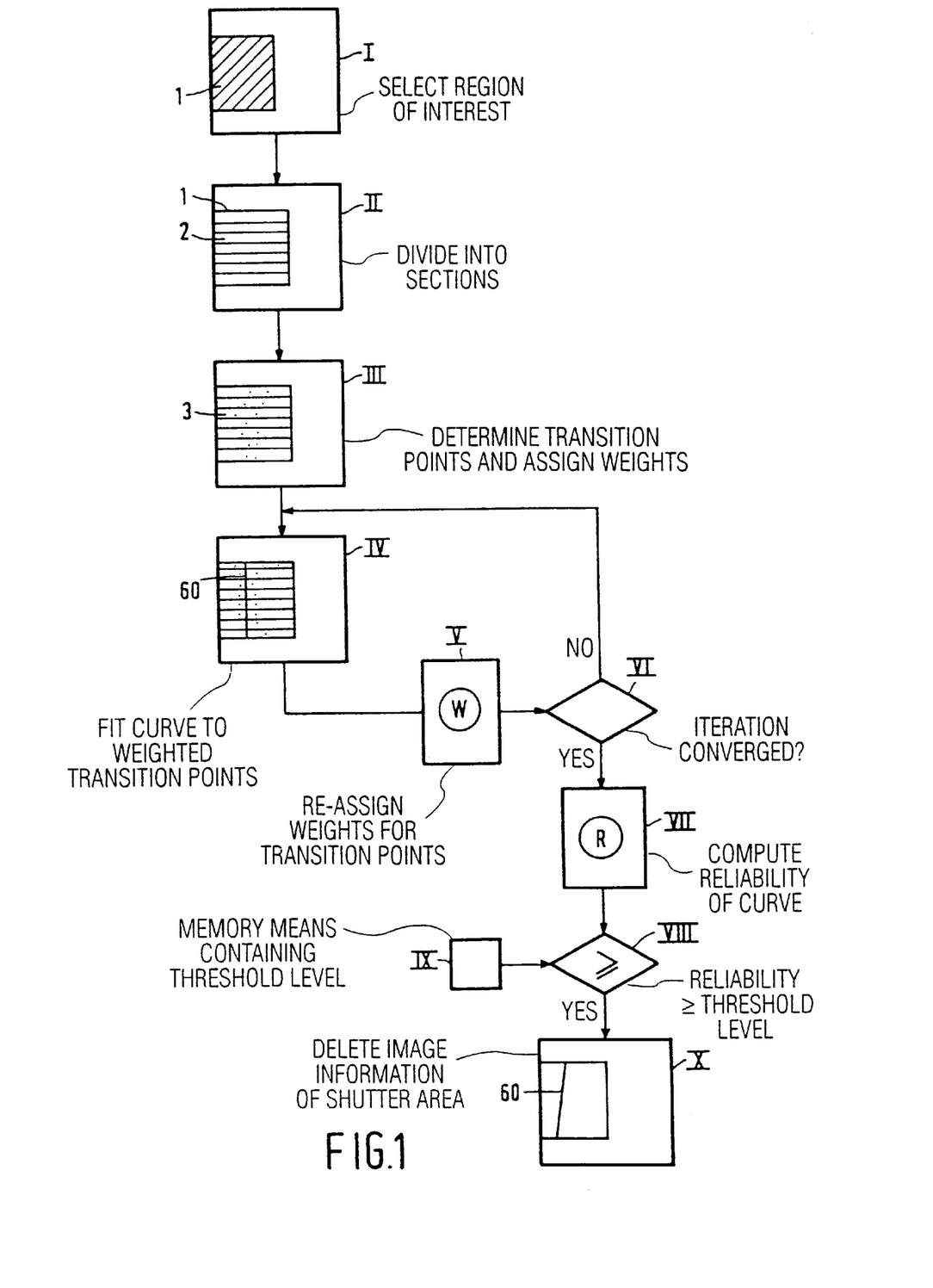
FIG. 1 shows a diagrammatic representation of an implementation of an image processing method in accordance with the invention.

FIG. 1 shows a diagrammatic representation of an image processing method in accordance with the invention. In block I a region of interest 1 is selected wherein an x-ray shutter-edge is expected. In block II said region of interest 1 is divided into sections 2. On the basis of brightness values in each of the sections 2, transition-points are determined, one of them being indicated by the reference numeral 3. Furthermore, weights are assigned to the transition-points and in block IV a curve is fitted through the transition-points where use is made of the weights for performing the curve fitting so as to obtain a fair representation of an x-ray shutter-edge. In block IV a fitted curve 60 is shown. Once a curve has been determined, further accuracy is achieved by computing weights for each of the transition-points where for a transition-point a weight is computed that depends on the distance between the fitted curve and said transition-point. Reassigning weights is performed in block V and the curve-fitting process is reiterated under control of a comparison step that is represented by block VI. When this iteration has converged, reliability of the converged curve is computed in block VII on the basis of the weight. In this way, because x-ray shutter-edges have transition-points that have comparatively high weights whereas anatomical structures have transition-points with lower weights, it is avoided to a large extent that anatomical structures are mistaken for an x-ray shutter-edge. To that end a computed reliability is compared in a comparison step represented by block VIII with a predetermined threshold level that is provided from a memory means IX. In a final step shown in block X, if the computed reliability measure is greater than or equal to the threshold level, image information of the x-ray shutter-area, being the area peripheral to the fitted curve, is deleted. The deletion may consist of setting all pixel-values on the x-ray shutter-area to a grey-level or a non-distracting colour-value that may be either predetermined or can be selected. Thus, said x-ray shutter-area is reduced in that image information of the x-ray shutter-areas is deleted. As an alternative the x-ray shutter-area is reduced in that said x-ray shutter-area is discarded from the image. If the computed reliability is less than the threshold level, the pixel values in the shutter-area remain unaltered.

Figure 2A:
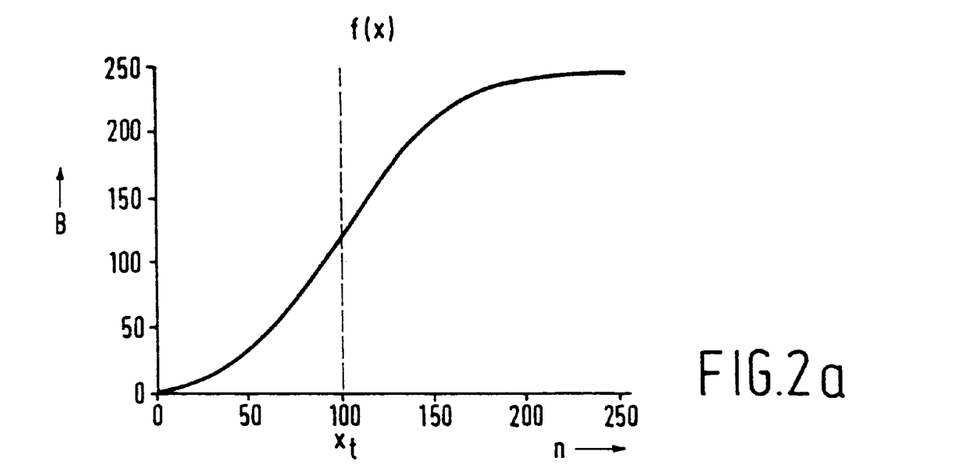
FIGS. 2a–c shows an exemplary variation of brightness around an x-ray shutter-edge, and first and second spatial derivatives of said variation.
Figure 2B:
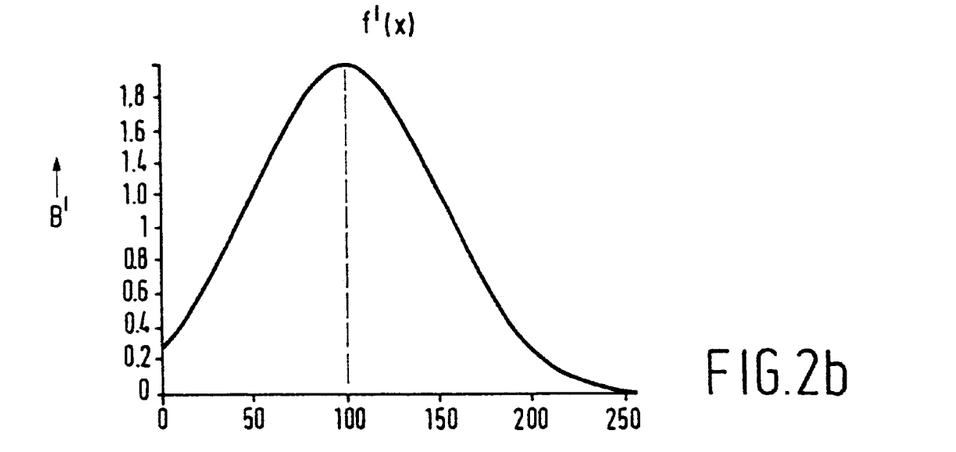
Figure 2C:
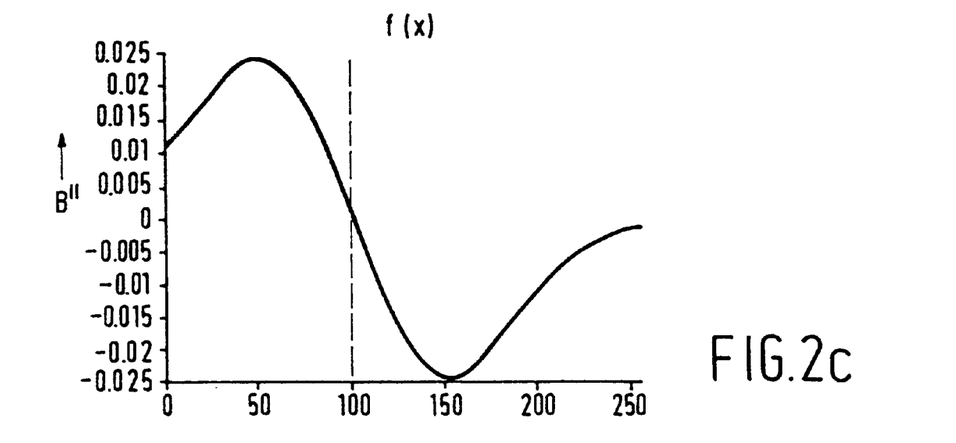

FIGS. 2a–c shows an exemplary variation of brightness around an x-ray shutter-edge, and first and second spatial derivatives of said variation. FIG. 2a shows dependence of brightness-values as a function of position along a line in an image made by x-ray exposure. The coordinate x increases from the periphery of the image towards the center of the image. As FIG. 2a shows the brightness-value B is very low near the periphery of the image owing to the presence of an x-ray shutter. There is a transition to high brightness-values around the position $\chi_t$ which is representative of the edge of an x-ray shutter. FIG. 2b shows the first spatial derivative $B'(\chi)$ in the direction of said line of the brightness variations shown in FIG. 2a. Notably, at the x-ray shutter-edge $\chi_t$ the derivative $B'$ has a maximum, indicating the brightness variations being the most pronounced at the x-ray shutter-edge. FIG. 2c shows the second spatial derivative $B''(\chi)$ in the direction of said line. As appears from FIG. 2c, the second derivative has a maximum close to the position $\chi_t$, where the first derivative has a maximum. In relation to the maximum of the first derivative, the maximum of the second derivative has a position that is towards the periphery of the image. The feature that the maximum of the first derivative at the side facing the periphery of the image is accompanied by a maximum of the second derivative, discriminates a brightness-transition having low brightness on the peripheral side and having high brightness on the side towards the center from a brightness-change having low brightness on the peripheral side and gradually increasing brightness towards the centre; such a brightness-change in practical situations often arises due to vignetting in the image.

Figure 3:
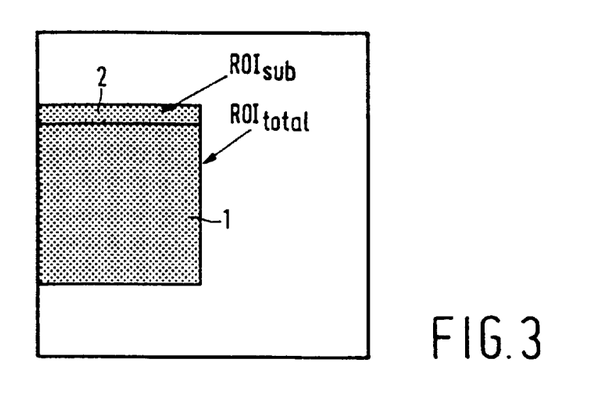
FIG. 3 shows a diagram of a division of a region of interest into sub-regions in accordance with the image processing method of the invention.

FIG. 3 shows a diagram of a division into sub-regions of a region of interest in accordance with the image processing method of the invention.

To search for an x-ray shutter-edge of an x-ray shutter located in the left part of the image first a region of interest $ROI_{total}$ 1 is selected as is indicated in FIG. 3. The region $ROI_{total}$ extends over half the vertical dimension of the image and from the left edge of to the middle of the image in the horizontal direction. In this manner, artifacts in the corners are left out of consideration and risk of conflict with other x-ray shutters being present is diminished. Other x-ray shutters, such as right-vertical, top-horizontal or bottom-horizontal can be detected in accordance with the invention by choosing regions replacing vertical and horizontal and top and bottom. Subsequently, the region $ROI_{total}$, which consists e.g. of 256×256 pixels is divided into elongated strips $ROI_{sub}$, one of them being shown of e.g. 256×32 pixels. For each of the strips pixel values are averaged in the vertical direction, i.e. to each of the 256 positions in the longitudinal direction of the strip currently being processed the average of the 32 pixel-values having the same horizontal position is assigned. This yields a dependence of (average) brightness along the elongated direction of the current strip, as is depicted e.g. in FIG. 2a.

Figure 4A:
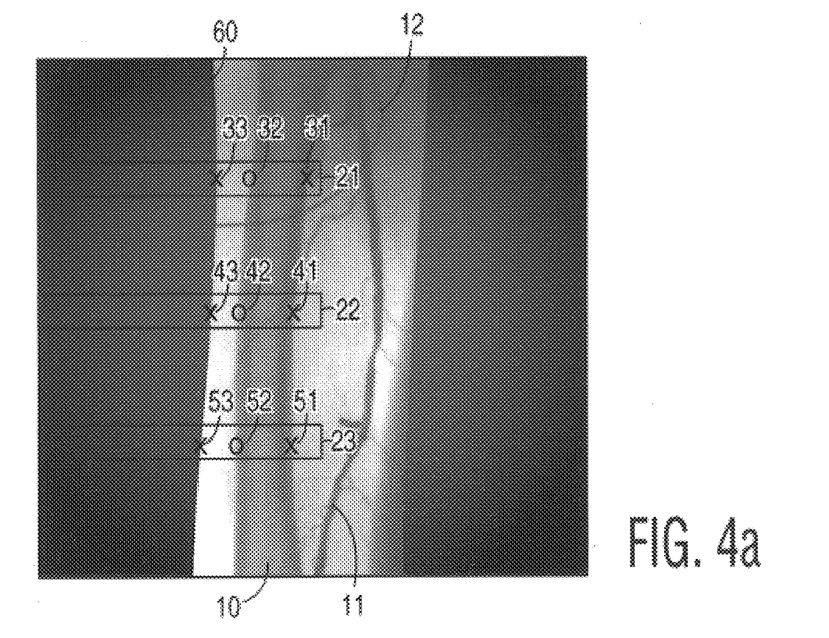
FIG. 4a shows a diagrammatic illustration of detection of x-ray shutter-edges in an image made by x-ray exposure.

FIG. 4a shows a diagrammatic illustration of detection of x-ray shutter-edges in an image made by x-ray exposure. FIG. 4a shows an image made by x-ray exposure featuring various anatomical structures such as a bone 10 and a artery 11 and a catheter 12. Furthermore, several elongated strips 21, 22 and 23, similar to the strips 2 in FIG. 3 are indicated. In each of the strips several brightness transitions occur. These brightness-transitions originate from either anatomical structures or from an x-ray shutter. E.g. in strip 21, at position 31 brightness changes from high to low when proceeding towards the periphery of the image, at position 32 the brightness B increases to a higher value and finally at position 33 brightness again drops to a very low value. Consequently, both brightness transitions at 31 and 33 are accompanied by respective maxima of the spatial derivatives B' and B", as discussed with reference to FIGS. 2a–c. On the other hand the brightness transition at position 32 is accompanied by a minimum of B', so that only the transitions at 31 and 33, respectively are considered candidates for a sought x-ray shutter-position. Because the transition at position 31 is accompanied by another transition being more peripheral, viz. the transition at position 33, to position 31 a smaller weight-factor is assigned and to the position 33 a large weight-factor is assigned.

Similarly, two further strips 22 and 23 are indicated, each of them comprising several brightness transitions at positions 41, 42, 43 and 51, 52, 53, respectively. Of these, the transitions at 43 and 53 are assigned a large weight-factor value. By a known curve-fitting method a curve 60 is drawn through the group of transition-points formed by (31, 33, 41, 43, 51, 53). The curve 60 forms a fair estimate of the x-ray shutter-edge of a left x-ray shutter.

The accuracy of the fitted curve which is representative for an x-ray shutter-edge is increased by iterating. After an estimate is obtained, weight-factors are reassigned to the positions that were used for obtaining the current fitted curve. The process is started by determining peak-points in each of the sections and choosing a curve that connects said peak-points as a first estimate for a curve representing an x-ray shutter-edge at issue. A peak-point is a transition-point such that the average distance between a predetermined number of neighboring transition-points and said peak-point is the smallest; empirically it has appeared that the choice of five neighboring transition-points is very adequate to determine a peak-point. When reassigning weight-factors, distances between said positions and the current fitted curve are taken into account such that positions that are close to the current fitted curve are given higher weight-factors than position that are more distant from the current fitted curve, for example by means of a Gaussian weight function. Then, on the basis of new values of weight-factors being assigned, again positions being most probable candidates for lying on an x-ray shutter-edge are selected and curve fitting is carried-out employing said new weight-factor values.

Still further refinement of the reliability of the image processing method in accordance with the invention is achieved by considering image features around a transition-point, i.e. a presumed x-ray shutter-edge. A first feature parameter of a brightness-transition is the height of the transition which is determined by the difference between averaged brightness values at the side of the transition towards the periphery of the image and averaged brightness at the side of the transition towards the center of the image. The averaging is e.g. performed over a predetermined number of pixels at a relevant side of a transition at issue.

A second feature parameter is the roughness of the image at the peripheral side of a brightness-transition at issue. In practical situations, x-ray shutters appear distinct from anatomical structures in that within an x-ray shutter-area there is very little structure; this is quantified by image roughness which is defined as the statistical variance of brightness-values in an area of the image at issue. An attractive alternative for quantifying roughness is obtained on the basis of second spatial derivatives of brightness which are interpreted as the difference between a local brightness-value and a running average built-up by three neighboring pixel-positions in total. Then roughness is defined quantitatively as a reciprocal of an average over the modulus of second spatial derivatives in an area of the image at issue. Low roughness values then correspond to an area of the image having little image structure, thus having a high probability of being an x-ray shutter-area. Further an image processing method in accordance with the invention is now refined in that weight-factors that are assigned to positions that are recognized as candidates for being on an x-ray shutter-edge are made increasing as a function of the height of the transition and are made decreasing as a function of the roughness in the area of the image peripheral of the candidate at issue.

Figure 4B:
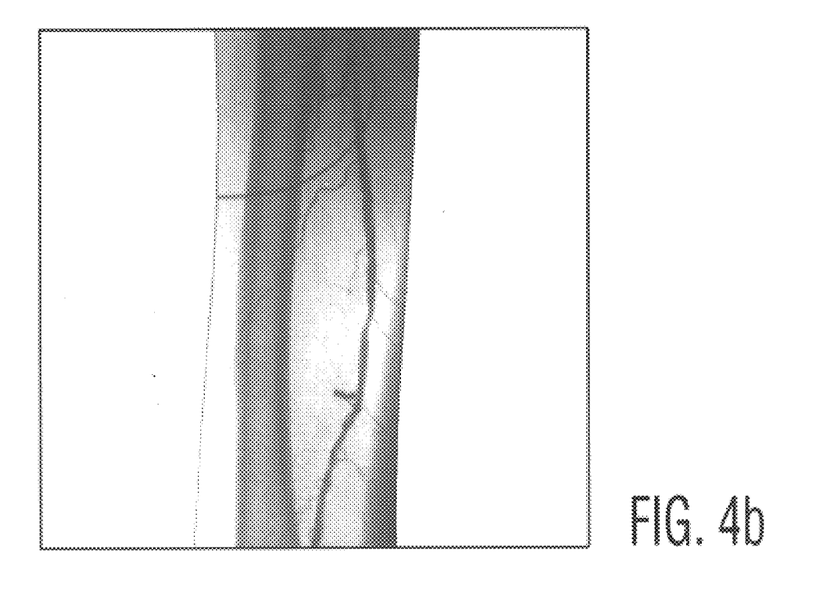
FIG. 4b shows a result of an image processing method in accordance with the invention having been applied to the image shown in FIG. 3b.

After all x-ray shutter-edges in the image have been determined, image-information in the areas of the image peripheral to any of the curves corresponding to x-ray shutter-edges is deleted from the image and as a result a processed image comprising only relevant medical information is obtained. In particular, in areas corresponding to x-ray shutters as determined according to the invention, all pixels are set to the same value; in this manner x-ray shutter-areas are blanked. FIG. 4b shows a processed image obtained from the image shown in FIG. 4b.

The processed image has as an advantage that it does not include parts that are distracting when examining the image. Furthermore, when a hard-copy e.g. on film of a plurality of images having been processed according to the invention is made, an advantage is achieved in that more economic use is made of hard-copy material.

Figure 5:
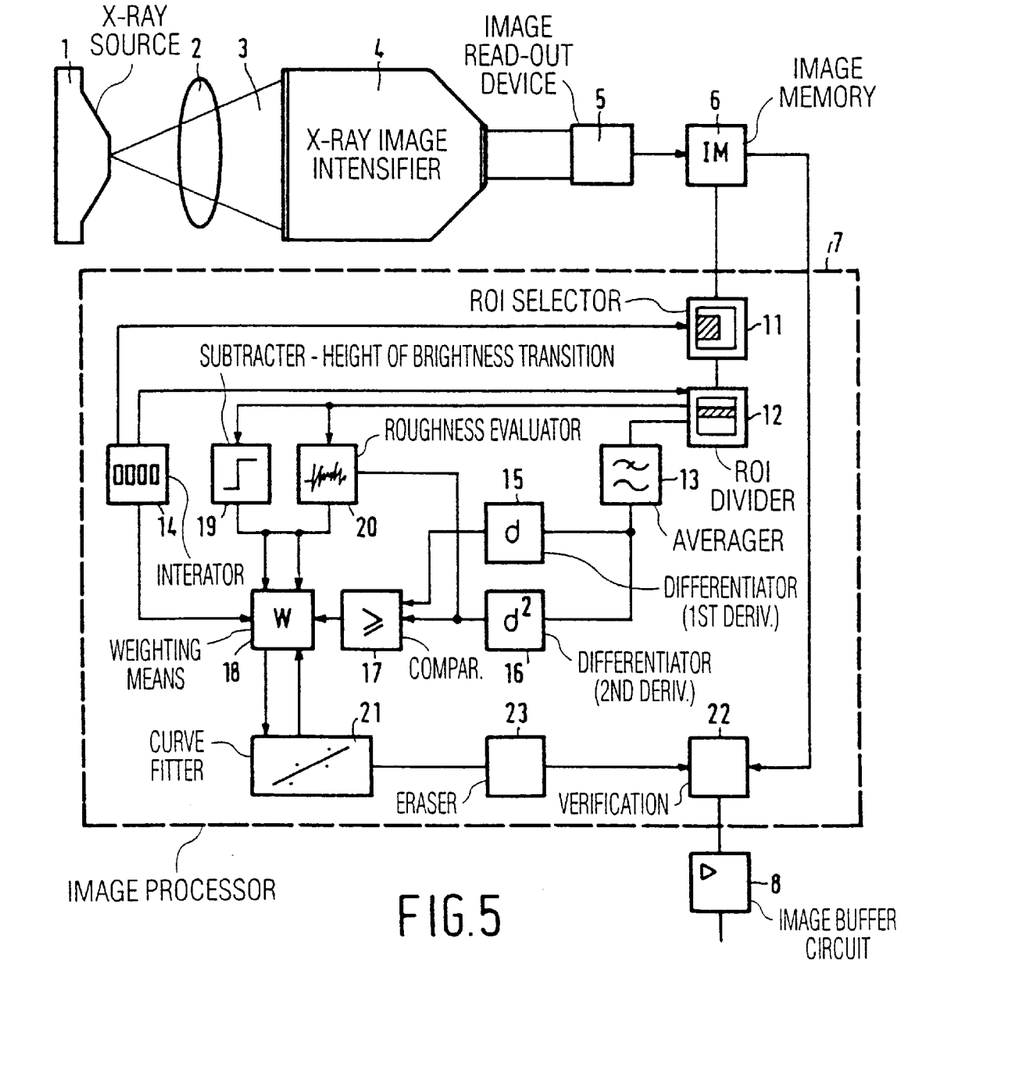
FIG. 5 shows a schematic representation of an x-ray examination apparatus comprising a device for performing an image processing method in accordance with the invention.

FIG. 5 shows a schematic representation of an x-ray examination apparatus comprising a device for performing the image processing method in accordance with the invention. An x-ray source 1 is provided for irradiating an object 2 so that an image carrying x-ray beam is formed. An x-ray absorption filter in the form of one or more x-ray shutters is interposed between the source 1 and the object 2 to intercept part of x-ray beam 3. By means of an x-ray detector 4 (an x-ray image intensifier as illustrated for producing an optical image) and an image read-out device 5 an image made by x-ray exposure is formed an supplied to an image-memory 6. An image processor 7 is employed for converting the image stored in the image-memory 6 into a processed image from which x-ray shutter-areas are deleted. The processed image is supplied to an image buffer-circuit 8 for further processing such as display on a monitor screen, formation of a hard-copy or to be archived.

The image processor 7 will now be described in more detail. A selector 11 selects a region of interest $ROI_{total}$ wherein an x-ray shutter-edge is to be detected. By a divider 12 the region of interest is divided into elongated strips $ROI_{sub}$. The selector 11 and the divider 12 are controlled by an iterator 14 for subsequently selecting said elongated strips for determining an x-ray shutter-edge and for subsequently selecting regions of interest for determining various x-ray shutter-edges. Brightness-values of pixels in an elongated strip are averaged along the transverse direction of the elongated strip at issue so that a one-dimensional brightness distribution being representative for image information along the longitudinal direction of the elongated strip, is formed by an averager 13. First and second spatial derivatives of the one-dimensional brightness distribution are computed by differentiators 15 and 16, respectively. From the output of the differentiators candidate-positions for x-ray shutter-edge positions are determined by a comparator 17. Weight factors are assigned to candidate x-ray shutter-edge positions by way of a weighting-means 18. Said weight-factors are computed by the weighting means 18. To that end the height of a brightness-transition at a positions at issue is computed by subtracter 19; the roughness associated to the brightness-transition at issue is computed by an evaluator 20. Through the candidate-x-ray shutter positions in successive elongated strips and using their associated weight-factors candidate x-ray shutter positions are selected and a curve is fitted by a curve-fitter 21. In addition to producing a curve that fits the selected positions, the curve-fitter computes updated weight-factors depending on the distances between respective selected positions and the fitted curve. Under control of the iterator 14, selection of candidate x-ray shutter-positions and subsequent curve-fitting is repeated so as to obtain a more reliable result for a curve being a fair approximation of an x-ray shutter-edge. The curve found after iteration has converged is supplied to a verification-means 22 to verify that said curve is indeed representative of an x-ray shutter-edge. The verification-means comprises a computation unit for calculating an average distance to a curve at issue of a predetermined number of transition-points. In particular five transition-points are chosen that have the smallest distances to the curve at issue. Moreover, the verification means comprises detection means for ascertaining that for a curve at issue, an x-ray shutter-edge is present in an opposite region of interest in the image. Subsequent to verification of approximating curves for various x-ray shutter-edges being present in the image stored in the image-memory 6, parts of the image being peripheral to any of said x-ray shutter edges are deleted by an eraser 23 and the processed image obtained in this manner is supplied to the image buffer-circuit 8.

It is noted that in an x-ray examination apparatus in accordance with the invention, the functions of the image processor may be performed by a suitably programmed computer or by a special purpose processor having circuit-means that are arranged to perform said functions.

Figure 6:
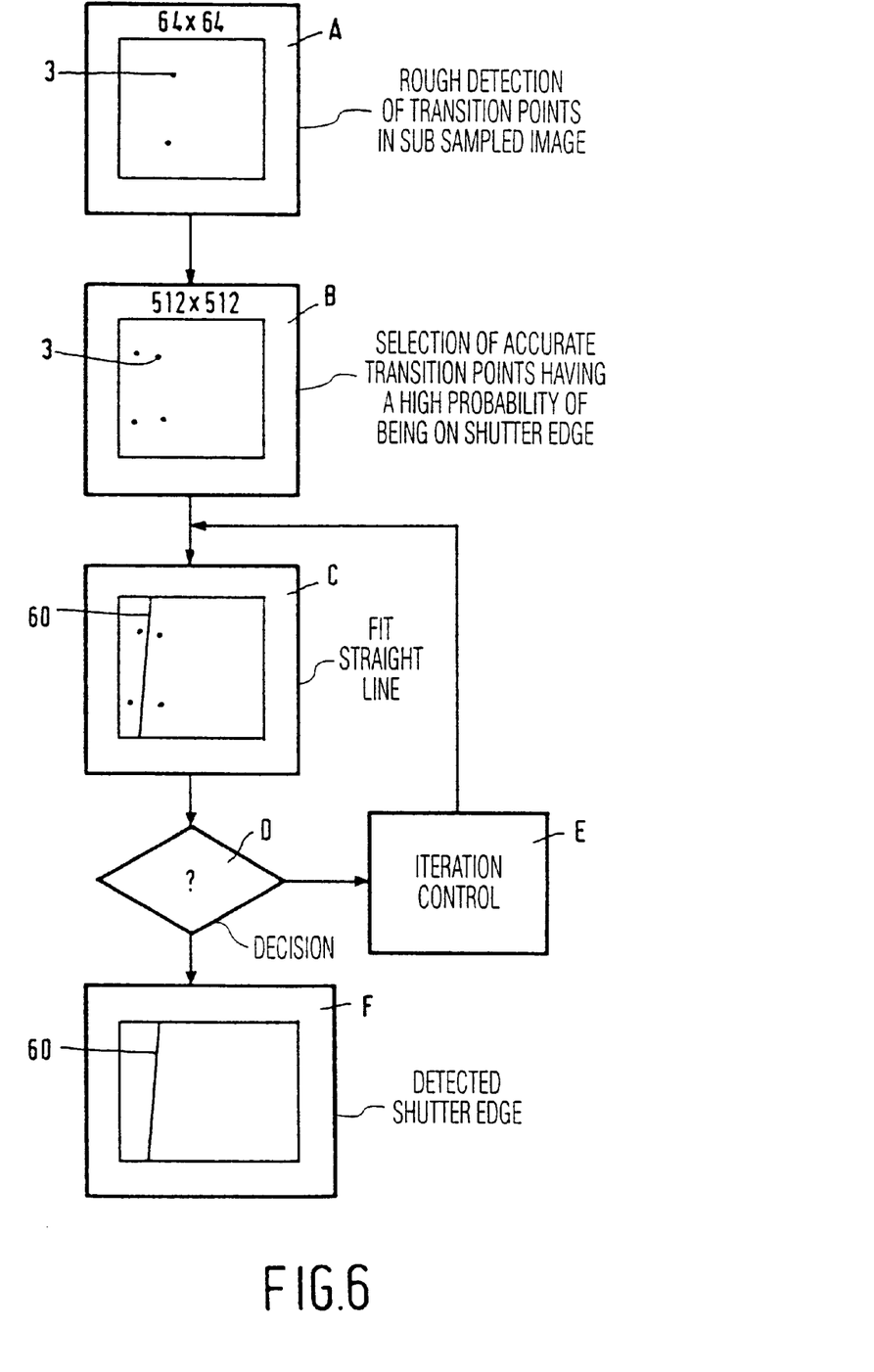
FIG. 6 shows a diagrammatic representation of a further implementation of an image processing method in accordance with the invention.

FIG. 6 shows a diagrammatic representation of a further implementation of an image processing method in accordance with the invention. In block A a rough detection of transition-points is performed. In this phase of the image processing method the full image having, for example, 512×512 pixels is subsampled down, for example, to 64×64 pixels by taking one point out of eight in the horizontal and vertical directions. This considerably reduces the computational burden at the cost of a lesser accuracy in localization of the transition-points. Accuracy will be recovered in the sequel of the image processing method, viz. in block B. The following computational steps are performed. The sub-sampled image is smoothed using a straight vertical kernel. This is done by adding to each pixel-value the pixel-value of pixels in the neighbourhood in said sub-sampled image. In this way, sharp horizontal transitions are retained in this way while vertical transitions are smoothed out.

Subsequently, nine rows are selected as sections, out of the 64 rows of the subsampled image. A systematic search for transition-points that lie on an x-ray shutter-edge is then performed. To that end, in each row the average pixel-value of pixels located between a transition-point and a periphery of the image is estimated by taking the sum of intensities of four pixels located between the pixel for which said average is to be computed and the periphery of the image. Next, the component in a direction orthogonal to a periphery of the image of a gradient of pixel-values is evaluated by computing differences between consecutive points in said section.

In block B accurate localisation of transition-points is represented. From the phase performed in block A, nine roughly localized transition-points are provided. The step of block B aims at increasing accuracy of localization of transition-points in the 512×512 image. A local search around each of said nine transition-points is performed within the same section for a neighborhood consisting of, for example, 17 pixels, viz. eight on either side of a transition-point at issue. The local search comprises smoothing in a direction parallel to said periphery of the image by adding pixel-values that neighbor the transition-point at issue in a direction parallel to said periphery. Subsequently, the sum is computed of four pixel-values of four pixels located between said periphery and the transition-point at issue, said sum being representative for an average brightness towards said periphery. A gradient in a direction orthogonal to said periphery is computed by calculating differences of pixel-values of the transition-point at issue and two of its neighbors that are located between said transition-point and the center of the image. Next, the ratio of said gradient and said average is computed for each transition-point in each of the sections. Accurate transition-points having a comparatively high probability for being on as x-ray shutter-edge are selected as those transition-points having a value for said ratio being the highest in said neighborhood of 17 pixels.

Block C represents the fitting of a curve, notably the best fit straight line through the accurate transition-points that are provided from the step of block B. Accurate transition-points which are comparatively far from said straight line are considered as outliers and are rejected. Alteratively, transition points can be weighted according to the distance to the curve, for example by a Gaussian weighting function. The computational procedure for the step of block C is iterative; it represents a compromise between accuracy and computation time optimization. The estimation of the x-ray shutter edge position in the image and angle with a predetermined axis of the image is then refined by determining the best fit straight line to the most likely accurate transition-points. For the following of the discussion, said predetermined axis will be chosen to be a vertical axis of the image, although the implementation is not at all restricted to this choice. The pixels of the image are arranged as a square matrix of columns and rows. The x-ray shutter-edge is first assumed to be vertical, its column number is taken to be that of the accurate transition-point with the largest number of substantially vertically aligned accurate transition-points. Each of the accurate transition-points is assigned a likelihood score. Let $\Delta\chi$ represent the maximum change in column number of a said accurate transition-points to account for a maximum angle departure of, for example, ±5° from a vertical edge. The likelihood score of any one of the accurate transition-points is calculated by adding up the number of accurate transition-points with column numbers differing by less than $\Delta\chi$ plus those with column number differing by less than $\Delta\chi/2$ plus those with column numbers differing by less than $\Delta\chi/4$. The first guess for the position of the x-ray shutter-edge is taken to be a vertical line at the column number of the accurate transition-point having the highest likelihood score. In practice $\Delta\chi$ is chosen to be a width of eight pixels.

To proceed further with a low computational burden and to decrease required computation time, accurate transition-points which lie comparatively far away from said guessed x-ray shutter edge position are rejected, for example according to the following test-rules. If four or more accurate transition-points are within a distance of $\Delta\chi/4$ from said guessed x-ray shutter-edge position then accurate transition-points having a distance larger than $\Delta\chi/2$ are rejected. If this test-rule does not apply, the test-rule is repeated after replacing the value of $\Delta\chi$ by $2\Delta\chi$. If neither of these test-rules apply, i.e. less than four accurate transition-points within a distance of $\Delta\chi$ from said guessed x-ray shutter-edge position, it is concluded that no x-ray shutter is present.

The accurate transition-points that have been retained after applying said test-rules are employed to more accurately localize the x-ray shutter-edge position in an iterative way under the control of an iteration control indicated as block E. The initial guess of the x-ray shutter-edge is a vertical line at the column number having the highest likelihood. For each of the retained accurate transition-points respective normal distances to said vertical line are computed and Gaussian weights depending on said normal distances are assigned such that the extreme points for an x-ray shutter having a tilt of 5° with the vertical axis are given weights of ½. The function of these weights is to diminish the influence of those retained accurate transition-points which are too poorly aligned with respect to others. A conventional least mean square regression is employed to determine a line that is representative for a new estimate of an x-ray shutter-edge position. In the iteration process, normal distances of retained accurate transition-points are recalculated for the new estimate for the x-ray shutter-edge position. Subsequently, new Gaussian weights are assigned where a Gaussian distribution with a smaller width is used. Following that, a new best fit straight line is determined, thus improving the estimate for the position of the x-ray shutter edge.

After a line that represents an x-ray shutter edge position has been provided by the steps of blocks C and E by iteration a decision-making step follows as is represented by block D. After the iteration has converged the root mean square distance $\Delta p$ of the retained accurate transition-points is calculated. The following situation may then occur. If $\Delta p$ is larger than 2.6 pixels it is decided that no x-ray shutter is present. The image processing method is then terminated. The value of 2.6 pixels has been determined empirically and may be different in other implementations or applications. If all nine accurate transition-points are retained and Δp is less than 1.2 pixels, it is decided that there is an x-ray shutter and the image processing method proceeds by reducing the area 61 that is peripheral to the line provided by the phase of block D. If only eight accurate transition-points are retained and Δp is less than 0.8 pixels it is also decided that there is an x-ray shutter and subsequently the x-ray shutter-area is reduced in block E. If none of the above mentioned situations occur the presence of an x-ray shutter is ambiguous and three further tests are performed in block D.

If such an ambiguous situations occurs, there are provided from previous phases a set of accurate transition-points. To save computation time further tests are carried-out using the 64×64 subsampled image. The mean pixel-value along two vertical line segments an inner one lying towards the center of the image and the other, outer one, lying towards said periphery are computed. The common length of these two line segments is taken to be slightly smaller than an estimated length of an x-ray shutter and to be compatible with the rounded shape of the x-ray image intensifier. A high mean pixel-value on the inner-segment and a low value on the outer-segment is compatible with the presence of an x-ray shutter. The quantity computed in this test is the ratio $R_{rl}$ of said two mean pixel-values and that quantity is compared with a predetermined reference value to decide on the presence of an x-ray shutter.

As a second test, the maximum value $L_{max}$ of the second spatial derivative (Laplacian) of the pixel-values on the outer segment. If this maximum value is found to be large, it indicates the presence of a anatomical structure towards the periphery of the accurate transition-point at issue and hence the likelihood of the presence of an x-ray shutter is reduced. A reliable criterion is a linear combination M of the ratio $R_{rl}$ and the maximum value $L_{max}$. The coefficients involved in this linear combination are those optimizing the statistical recognition results on the part of the image used for training the algorithm. The linear combination M is compared to a predetermined reference value so as to decide on the presence of an x-ray shutter.

A final independent test that is used in an ambiguous situation also aims at rejecting false x-ray shutter detections. In this final independent test the maximum negative slope on a line orthogonal to said periphery of an image is computed between an accurate transition-point at issue and said periphery. If this maximum negative slope is larger than a predetermined reference value it is decided that no x-ray shutter is present. As pixel values hardly ever decrease strongly in a direction of an x-ray shutter, considering said maximum negative slope constitutes a reliable test for the presence of an x-ray shutter in an ambiguous situation. Strongly decreasing pixel-values peripheral from the computed curve therefore indicate that the computed curve does not represent an x-ray shutter-edge.

We claim:

1. An image processing method to process an image which is formed by x-ray imaging and stored in an image memory, the stored image after completion of its formation by x-ray imaging containing a portion corresponding to an x-ray absorption filter, which image processing method comprises determining from the stored image an edge of said portion, and utilizing the determined edge, forming a modified image from the stored image by selectively processing said portion to be non-distracting by removing all information content in said portion such that the modified image has no information content in said portion.

2. An image processing method as claimed in claim 1, wherein the selective processing comprises removing substantially said entire portion from the stored image.

3. An image processing method as claimed in claim 1, wherein the selective processing comprises assigning a same uniform value to pixels in substantially said entire portion in the stored image.

4. An image processing method as claimed in claim 1, wherein the determining an edge comprises:

a grouping step to select a group of transition-points in the image having a higher brightness towards the center of the image and a lower brightness towards the periphery of the stored image, and a curve-fitting step to fit a curve through said group of transition-points, said curve forming a representation of said edge.

5. An image processing method as claimed in claim 4, wherein the grouping step comprises:

a region-selection step to select a region of interest extending from a periphery of the image, a division-step to divide said region of interest into sections, and a weight-assignment step to assign weights to said transition-points, a weight for a transition-point depending on image features around said transition-point and a weight for a transition-point depending decreasingly on a distance between said transition-point and said periphery.

6. An image processing method as claimed in claim 5, wherein the grouping step comprises a first-estimate step to determine a first-estimate for a position of a transition-point in a section and a step to determine more accurately the transition-point from said first-estimate.

7. An image processing method as claimed in claim 5, wherein the weight-assignment step comprises:

computation of first and second spatial derivatives of brightness-values near respective transition-points, and employing substantial concurrence of a maximum of said first derivative with a brightness-variation and with a maximum of said second derivative at the peripheral side of said brightness-variation for selecting the position of said brightness-variation as a transition-point and assigning said weight on the basis of said concurrence.

8. An image processing method as claimed in claim 5, wherein the weight assignment step is followed by a point-selection step for selecting a transition-point having the highest weight in a section and retaining only said selected transition-points in said selected group.

9. An image processing method as claimed in claim 4, wherein determining an edge is followed by an edge-verification step comprising computation of a reliability-parameter for an edge being determined and comparison of said reliability-parameter with a predetermined threshold level.

10. An image processing method as claimed in claim 9, wherein for a plurality of transition-points said reliability parameter is computed and where comparison of said reliability parameter to said predetermined reference level indicates the presence of said portion corresponding to an x-ray absorption filter for fewer transition-points than a predetermined reference number the edge-verification step is supplemented by comparison of pixel-values of collections of pixels on different sides of the curve.

11. An image processing method as claimed in claim 9, wherein for a plurality of transition-points said reliability parameter is computed and where comparison of said reliability parameter to said predetermined reference level indicates the presence of said portion corresponding to an x-ray absorption filter for fewer transition-points than a predetermined reference number the edge-verification step is supplemented by determining a magnitude of a first spatial derivatives of brightness-values of pixels in the stored image between the curve and the periphery of the stored image, said derivative being negative in the direction from the curve to the periphery of the stored image and comparing said magnitude to a predetermined reference value.

12. An image processing method as claimed in claim 6, wherein the weight-assignment step comprises:

computation of image roughness, computation of transition-height, and computation of said weights depending on image roughness and transition height for respective transition-points.

13. An image processor to process an image which is formed by x-ray imaging and stored in an image memory, which image after completion of its formation by x-ray imaging contains a portion corresponding to an x-ray absorption filter, comprising means for determining from the image an edge of said portion and means, utilizing the determined edge, for forming a modified image from the stored image by selectively processing said portion to be non-distracting by removing all information content from the stored image in said portion such that the modified image has no information content from the stored image in said portion.

14. An x-ray examination apparatus comprising an x-ray absorption filter between an x-ray detector and an x-ray source for irradiating an object to form an x-ray image on the x-ray detector, comprising an image processor according to claim 13 and having an input port coupled to the x-ray detector.

15. An image processing method to process an image which is formed by x-ray imaging and stored in an image memory, the stored image after completion of its formation by x-ray imaging containing a portion corresponding to an x-ray absorption filter, which image processing method comprises:

determining from the stored image an edge of said portion, wherein said determining comprises a region-selection step to select a region of interest extending from a periphery of the image, a division-step to divide said region of interest into sections, a weight-assignment step to assign weights to one or more transition-points determined in each region, a weight for a transition-point depending on image features around said transition-point and a weight for a transition-point depending decreasingly on a distance between said transition-point and said periphery, a grouping step to select a group of transition-points in the image according to the assigned weight to have a higher brightness towards the center of the image and a lower brightness towards the periphery of the stored image, and a curve-fitting step to fit a curve through said group of transition-points, said curve forming a representation of said edge, and utilizing the determined edge, forming a modified image from the stored image by selectively processing said portion to be non-distracting by removing substantially all information content in said portion such that the modified image has substantially no information content in said portion.

16. An image processing method as claimed in claim 15, wherein the weight-assignment step comprises:

computation of image roughness, computation of transition-height, and computation of said weights depending on image roughness and transition height for respective transition-points.

17. An image processing method as claimed in claim 15, wherein the weight-assignment step comprises:

computation of first spatial derivatives of brightness-values peripheral to respective transition-points, computation of respective average brightness-value of pixels towards the center to said transition-points, computation of respective ratios of said respective first spatial derivatives and said respective average brightness-values, and assigning said weights on the basis of said ratios.

18. An image processing method as claimed in claim 15, wherein the curve-fitting step is followed by a reassigning step for reassigning a value to a weight of a transition-point in dependence on a distance between said transition-point and a curve fitted through the group whereto said transition-point belongs, and in that the curve-fitting step is reiterated employing said reassigned weight.

19. An image processing method as claimed in claim 15, wherein the weight-assignment step comprises:

computation of first and second spatial derivatives of brightness-values near respective transition-points, and employing substantial concurrence of a maximum of said first derivative with a brightness-variation and with a maximum of said second derivative at the peripheral side of said brightness-variation for selecting the position of said brightness-variation as a transition-point and assigning said weight on the basis of said concurrence.

20. An image processing method to process an image which is formed by x-ray imaging and stored in an image memory, the stored image after completion of its formation by x-ray imaging containing a portion corresponding to an x-ray absorption filter, which image processing method comprises:

determining from the stored image an edge of said portion, wherein said determining comprises a grouping step to select a group of transition-points in the image having a higher brightness towards the center of the image and a lower brightness towards the periphery of the stored image, and a curve-fitting step to fit a curve through said group of transition-points, said curve forming a representation of said edge, verifying the determined edge by computation of a reliability-parameter for an edge being determined and comparison of said reliability-parameter with a predetermined threshold level, wherein the comparison indicates the presence of said portion corresponding to an x-ray absorption filter for fewer transition-points than a predetermined reference number the edge-verification step is supplemented by comparison of pixel-values of collections of pixels on different sides of the curve, and utilizing the determined edge, forming a modified image from the stored image by selectively processing said portion to be non-distracting by removing substantially all information content in said portion such that the modified image has substantially no information content in said portion.

21. An image processing method to process an image which is formed by x-ray imaging and stored in an image memory, the stored image after completion of its formation by x-ray imaging containing a portion corresponding to an x-ray absorption filter, which image processing method comprises:

determining from the stored image an edge of said portion, wherein said determining comprises a grouping step to select a group of transition-points in the image having a higher brightness towards the center of the image and a lower brightness towards the periphery of the stored image, and a curve-fitting step to fit a curve through said group of transition-points, said curve forming a representation of said edge, verifying the determined edge by computation of a reliability-parameter for an edge being determined and comparison of said reliability-parameter with a predetermined threshold level, wherein the comparison indicates the presence of said portion corresponding to an x-ray absorption filter for fewer transition-points than a predetermined reference number the edge-verification step is supplemented by determining a magnitude of a first spatial derivatives of brightness-values of pixels in the stored image between the curve and the periphery of the stored image, said derivative being negative in the direction from the curve to the periphery of the stored image and comparing said magnitude to a predetermined reference value, and utilizing the determined edge, forming a modified image from the stored image by selectively processing said portion to be non-distracting by removing substantially all information content in said portion such that the modified image has substantially no information content in said portion.

* * * * *